United States Patent [19]
Morris, Jr. et al.

[11] Patent Number: 5,498,428
[45] Date of Patent: Mar. 12, 1996

[54] TREATMENT OF HYPERTENSION BY ORAL ADMINISTRATION OF POTASSIUM BICARBONATE

[75] Inventors: R. Curtis Morris, Jr.; Anthony Sebastian, both of San Francisco, Calif.

[73] Assignee: The Regents of the University of California, Oakland, Calif.

[21] Appl. No.: 186,257

[22] Filed: Jan. 10, 1994

Related U.S. Application Data

[63] Continuation of Ser. No. 708,827, May 29, 1991, abandoned, which is a continuation of Ser. No. 577,846, Aug. 31, 1990, abandoned, which is a continuation of Ser. No. 420,596, Oct. 17, 1989, abandoned, which is a continuation-in-part of Ser. No. 260,856, Oct. 21, 1988, abandoned.

[51] Int. Cl.$^6$ .............................. A01N 59/00; A61K 33/00
[52] U.S. Cl. ............... 424/717; 424/722; 128/672
[58] Field of Search ........................ 424/717, 722; 128/672

[56] References Cited

U.S. PATENT DOCUMENTS

| | | |
|---|---|---|
| 3,708,574 | 1/1973 | Corker. |
| 4,216,237 | 8/1980 | Smith ........................ 426/806 |
| 4,259,315 | 3/1981 | Lippmann. |
| 4,405,596 | 9/1983 | Helbig et al. ............... 424/478 |
| 4,855,289 | 8/1989 | Wester. |

OTHER PUBLICATIONS

New England Journal of Medicine Jun. 1994 No. 25 Vol. 330 pp. 1776–1781.
Chem. Ab. 85:60772t 1976 Young et al.
Siani et al. Brit. Med. J. 294: pp. 1453–1456, 1987.
Cappuccio et al. J. of Hypertension 1991 9:465–473.
Smith et al., Br. Med. J., 290:110–112, (1985).
Sugimoto et al., Hyperten. 11:579–585, (1988).
Suppa et al., J. Hyperten. 6:787–790, (1988).
Tannen, Annals of Int. Med., 98 (Part 2): 773–780, (1983).
Tannen, Kid Int. 32(S22):242–248, (1987).
Tobian et al., (I) Hypertension. 6 (supp I): I–170–I–176, (1984).
Tobian (II) J. Hyperten. 4 (Supp 4): S67–S76, (1986).
Tobian (III), Can. J. Physiol. Pharmacol. G4:840–848, (1986).
Tobian (IV), Nutr. Rev. 46(8):273–283, (1988).
Treasure et al., Hyperten. 5:864–872, (1983).
Ullian et al., Sem. Nephr. 7(3):239–252, (1987).
Witzgall et al., J. of Hypertens., 4:201–205, (1986).
Zoccali et al., J. of Hypertens., 3(1):67–72, (1985).
Cappuccio et al., J. of Hypertens. 9(5):465–473, (1991).
Overlack et al., Klin Wochenschr, 69(Supp XXV): 79–83 (1991).
Beilin, Clin. and Exper'tal Pharm. and Phys., 15:215–23, (1988).
de Wesselow et al., Quart. J. Med., 8:361–374, (1939).
Kolata, Science, 218:361–62, (1982).
Luft et al., Am. J. Clin. Nutr., 45:1289–94, (1987).
Maxwell et al., Med. Clinics N. America, 71(5):859–874, (1987).
Miller et al. (I), Hyperten. 10:437–442, (1987).
Miller et al., (II)., Clin. and Exper. Theor. and Prac. A8 (4 and 5): 823–827, (1986).
Priddle, Can. Med. Assoc. J. 25:5–8, (1931).
Singh et al., Acta. Cardiologica. XLII:103–113, (1987).
Skrabal et al., Clinical Science 59:157s–160s, (1980).
Skrabal et al., The Lancet, 895–900, (1981).

(List continued on next page.)

Primary Examiner—Peter F. Kulkosky
Attorney, Agent, or Firm—Townsend and Townsend and Crew

[57] ABSTRACT

Novel methods are provided for treating hypertension in humans which comprise administering therapeutic amounts of pharmaceutically-acceptable non-halide salts of potassium. Preferred salts are potassium bicarbonate and potassium phosphate. The methods may also be used to lower the blood pressure of normotensive individuals. Dietary supplementation is a preferred and convenient method of administration.

26 Claims, 2 Drawing Sheets

OTHER PUBLICATIONS

Morgan, T. "Hypertension Treated By Salt Restriction", *The Lancet*, Feb. 4, 1978, pp. 227–230.

Morgan, "The effect of potassium and bicarbonate ions on the rise in blood pressure caused by sodium chlorides", *Clin. Sci.* 63:407s–409s (1982).

Myers J., Morgan T., "The Effect of Sodium Intake on The Blood Pressure Related to Age and Sex", *Clin. and Exper. Hyper. Theory and Practice*, A5(1), 99–118 (1983).

Morgan T. et al., "The Role of Potassium in Control of Blood Pressure", *Drugs* 28: Suppl. 1, pp. 188–195 (1984).

Morgan, T. et al. "The role of sodium restriction in the management of hypertension", *Can. J. Physiol. Pharmacol.* vol. 64, 1986.

Morgan et al., "Factors That Determine The Response Of People With Mild Hypertension To A Reduced Sodium Intake", *Clin. and Exper.–Theory and Practice*, A8(6), pp. 941–962, (1986).

Morgan, T. et al., "Compliance and the Elderly Hypertensive", *Drugs* 31 (Suppl. 4) pp. 174–183 (1986).

Chalmers, et al., "Australian National Health and Medical Research Council Dietary Salt Study in Mild Hypertension", *J. of Hypertension* 4 (Suppl. 6):S629–S637 (1986).

Morgan et al., "Comparative Studies of Reduced Sodium and High Potassium Diet in Hypertension", *Nephron* 47: Suppl. 1, pp. 21–26 (1987).

Nowson, Morgan, "Change in Blood Pressure in Relation to Change in Nutrients Effected By Manipulation of Dietary Sodium and Potassium", *Clinical and Experimental Pharmacology & Physiology* 15, pp. 225–242 (1988).

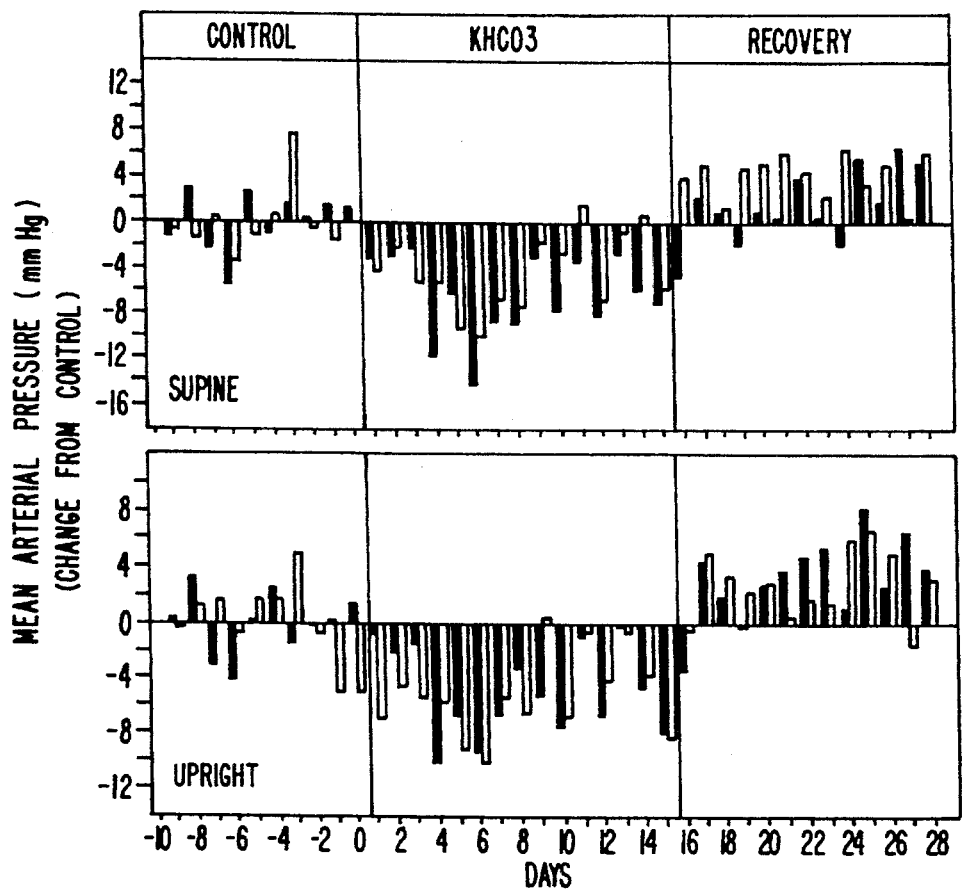
FIG._1.
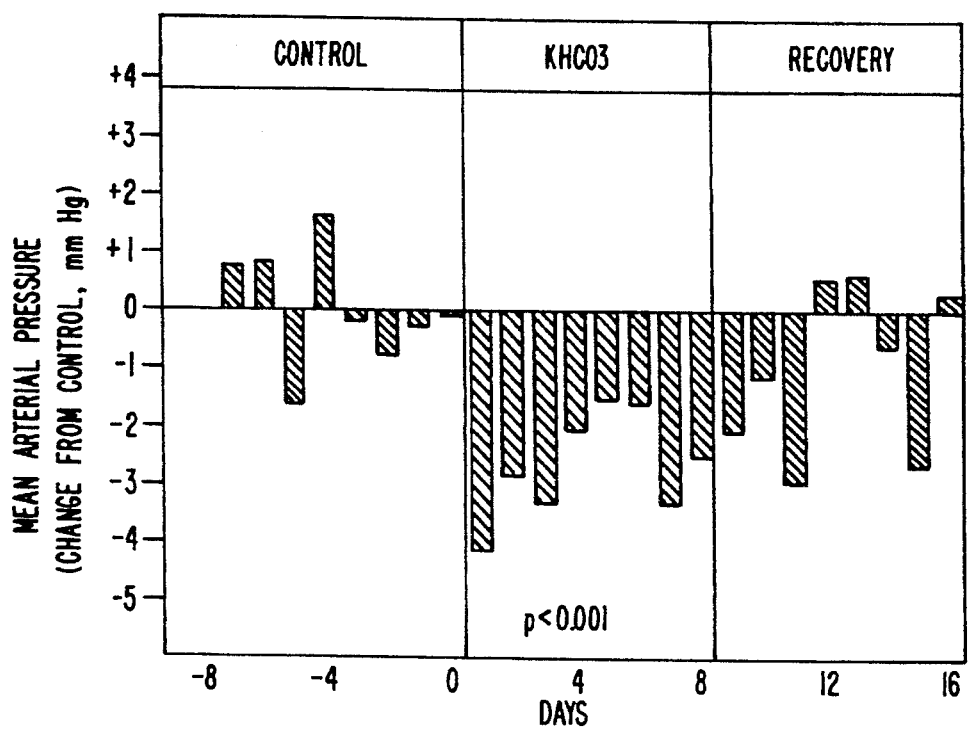
FIG._2.

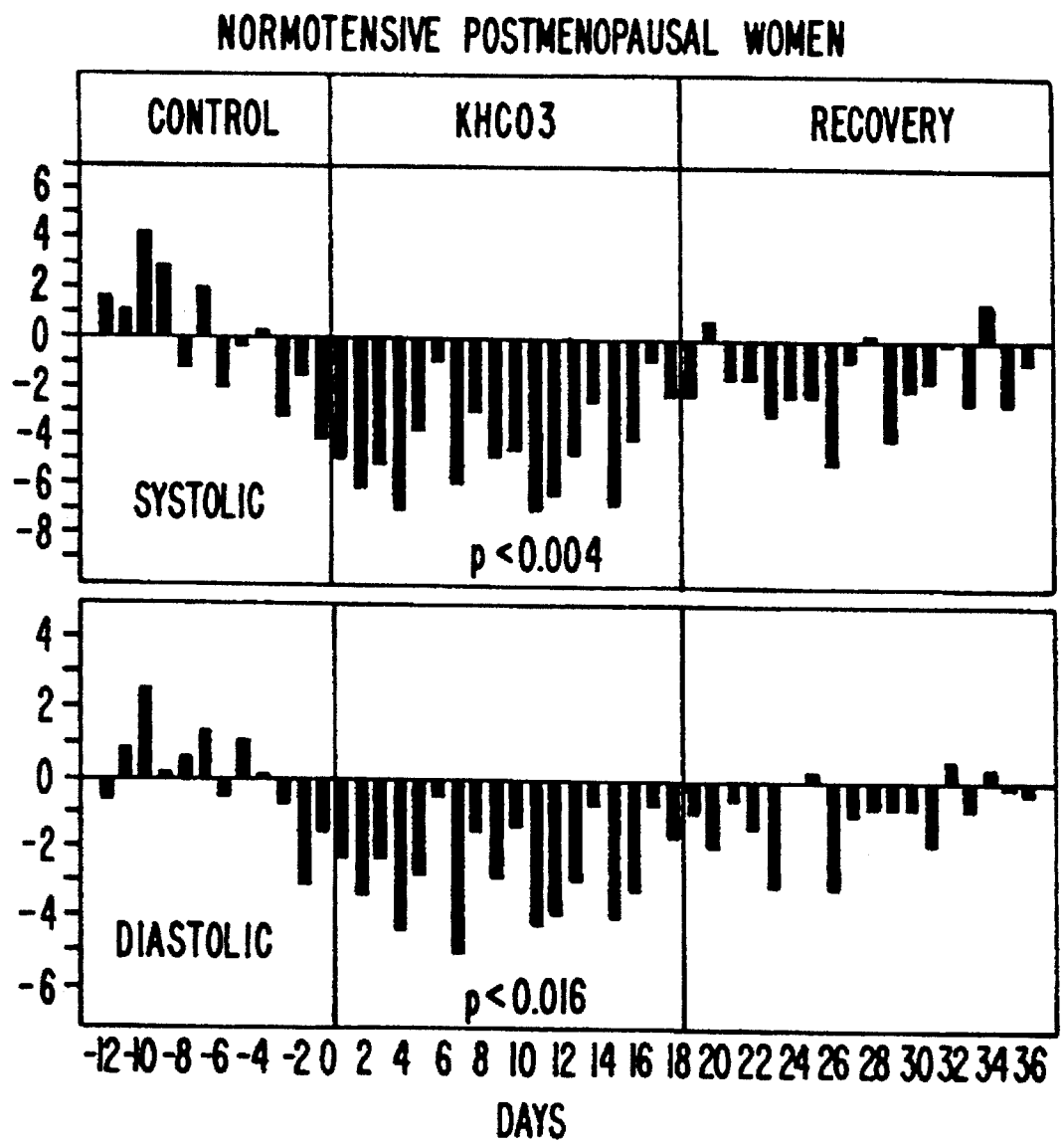
FIG._3.

TREATMENT OF HYPERTENSION BY ORAL ADMINISTRATION OF POTASSIUM BICARBONATE

GOVERNMENT SUPPORT

This invention was made with Government support under Grant No. M01-RR0079 awarded by the National Institutes of Health. The Government has certain rights in this invention.

This is a continuation of application Ser. No. 07/708,827, filed May 29, 1991, now abandoned, which is a continuation of application Ser. No. 07/577,846, filed Aug. 31, 1990, now abandoned which is a continuation of application Ser. No. 07/420,596, filed Oct. 17, 1989, now abandoned which is a continuation-in-part of U.S. patent application Ser. No. 260,856, filed Oct. 21, 1988 now abandoned.

FIELD OF THE INVENTION

This invention concerns novel methods for treating and diagnosing hypertension in humans and, more particularly, involves administration of pharmaceutically-acceptable non-halide potassium salts, such as potassium bicarbonate, in a variety of dietary and pharmaceutical compositions.

BACKGROUND OF THE INVENTION

Hypertension is an insidious disease which affects many people. Hypertension is generally defined as an abnormally increased blood pressure. It is clinically recognized as an elevation of systolic arterial blood pressure of 150 mm Hg or greater and/or an elevation of diastolic arterial blood pressure of 90 mm Hg or higher. Certain risk factors, e.g., hypercholesterolemia, diabetes, smoking, and a familial history of vascular disease, in conjunction with hypertension may predispose individuals to arteriosclerosis and consequent cardiovascular morbidity and mortality.

During the past three decades, morbidity and mortality resulting directly or indirectly from hypertension have fallen with the development of effective pharmacological agents. Several anti-hypertensive drugs that act predominantly on the peripheral sympathetic nervous system, adrenergic receptors, autonomic ganglia, and/or on the renin-angiotensin system have been described and include, for instance, propranolol, methyldopa, clonidine, and prazosin, to name but a few. Diuretic agents have also become a mainstay in anti-hypertensive therapy, and include thiazides and closely related phthalimidine derivatives, e.g., chlorthalidone. Others, such as hydralazine, act as vasodilators by causing the direct relaxation of arteriolar vascular smooth muscle.

In general, however, drug therapy for hypertension is reserved for those individuals whose blood pressure cannot be maintained in an acceptable range by non-pharmacological means. Of the non-pharmacological treatments for hypertension, weight reduction and salt (sodium chloride) restriction have been considered to be the most successful. Restricting dietary salt, although of somewhat limited and unpredictable effect, can in some cases reduce diastolic blood pressure to an extent comparable to that achieved by treatment with some of the pharmacologic agents.

Patients whose cause of hypertension is not readily apparent are said to have "essential hypertension." This group comprises approximately 95% of the patients treated for hypertension. Patients with essential hypertension whose blood pressure decreases with restriction of dietary sodium chloride and increases with its subsequent supplementation are characterized as having "salt-sensitivity" or, more precisely, "sodium chloride-sensitive" hypertension. Fujita et al., Am. J. Med. (1980) 69:334 and Kurtz et al., N. Engl. J. Med. (1987) 317:1043. Certain elements of the population have been reported to be more salt-sensitive than others, and thus exhibit greater blood pressure changes when subjected to different dietary intakes of NaCl (see, for example, Weinberger, et al., J. Am. Coll. Nutr. 1:139–148, 1982; Luft, et al., Am. J. Med. 72:726–736, 1982; Dustan, et al., Am. J. Med. Sci. 295:378–383, 1988; and Sullivan, et al., Am. J. Med. Sci. 295:370–377, 1988.

The prevalent view is that the capacity of sodium chloride to increase blood pressure depends only on its sodium component and that, hence, all commonly ingested sodium salts have this capacity (Sodium and Potassium in Foods and Drugs: NAK Conference Proceedings, White and Crocco, eds., Amer. Med. Assn., Chicago, 1980; Willis, ed., FDA Drug Bulletin (1983) 13:25). A standard pharmacological textbook, Goodman and Gilman, The Pharmacological Basis of Therapeutics, 7th Ed., 1985, recommends that sodium restriction should be encouraged for hypertensive patients and used as a definitive therapy if effective.

Some studies have suggested that the anion component of a dietary sodium salt may determine the extent to which that sodium salt induces an increase in blood pressure. Kurtz et al., Science (1983) 222:1139; Whitescarver et al., Science (1984) 223:1430; and Kurtz et al., New Engl. J. Med., (1987), 317:1043. These studies suggest that both the sodium and chloride ions of NaCl are required for its capacity to increase blood pressure.

The results of clinical and epidemiological studies suggest that the amount of potassium in the diet may also be an important determinant of blood pressure in patients with hypertension and, in some instances, in normotensive subjects. It has been observed that increasing potassium intake by the administration of a dietary supplement of potassium tends to lower blood pressure. (Addison, et al., Can. Med. Assoc. 18:281–285, 1928; Morgan, et al., Clin. Sci. 63:407s–409s, 1982; Holly, et al., Lancet 2:1384–1387, 1981; Fujita, et al., Hypertension 6:184–192, 1984; MacGregor, et al., J. Cardiovasc. Pharmacol. 6:S244–S 249, 1984, Siani et al., Br. Med. J. 294:1453–1456; and Obel, J. Cardiovasc. Pharmacol. 14:294–296, 1989). The anti-hypertensive effect of increasing potassium intake, however, has usually been small and variable.

In one experimental program, the blood pressure-lowering effect of dietary potassium supplementation was insignificant in patients on moderately restricted NaCl diets. Smith, et al., Br. Med. J. (1985) 290:110. Indeed, no anti-hypertensive effect of potassium was observed in studies by some investigators. See, Richards et al., Lancet (1984) 1:757 and Skrabal et al., Klin. Wochenschr. (1984) 62:124.

The possible use of a potassium salt other than potassium chloride, namely potassium citrate, to treat hypertension has also been suggested in the technical literature. Addison, Id. In that report, summarizing experiments on five subjects on "salt-poor diets" potassium citrate was said to exhibit a blood pressure lowering effect. Addison claimed that potassium citrate was more effective than potassium chloride in two of the three patients in whom he compared the hypotensive effect of the two potassium salts. In neither of these two instances, however, does the reported data justify the claim that potassium citrate was more effective than potassium chloride in reducing blood pressure. Indeed, to our knowledge, potassium citrate has not been recommended as a therapy for hypertension in any publication in the medical literature in the sixty years since the date of the Addison paper.

What is still urgently needed is an effective method for treating essential hypertension which utilizes a potassium compound that may be conveniently administered, preferably as a dietary supplement, which avoids concomitant administration of chloride, which is relatively easy to manufacture in bulk, and which may be made available at comparatively low cost. The present invention fulfills these and other related needs.

SUMMARY OF THE INVENTION

The present invention involves a novel method for ameliorating or preventing hypertension in humans afflicted with or predisposed to hypertension, which method comprises administering a therapeutically- or prophylactically-effective amount of a composition of a pharmaceutically-acceptable potassium salt in which the anion component is not a chloride or other halide. The potassium salt may be selected from the group consisting of potassium bicarbonate, potassium phosphate, or an alkalinizing potassium salt of a carboxylic acid, e.g., potassium gluconate and potassium citrate, among others. In particularly preferred embodiments the salts are potassium bicarbonate and potassium phosphate.

The non-halide potassium salt may be administered to ameliorate or prevent hypertension in any of several therapeutically- or prophylactically-acceptable forms and by a variety of routes. The compositions may conveniently be formulated and administered as a dietary supplement. An effective dosage of potassium bicarbonate is typically about 50–250 millimoles (mmoles) per 70 kg body weight per day.

In accordance with this invention it is particularly preferred to administer the non-halide potassium salt as a dietary supplement to patients on nutritionally adequate whole-foods diets that have "normal" salt (NaCl) contents (about 75 to 300 meq. of Na per day). It has been found that administration of the potassium salt in this way is particularly effective in ameliorating hypertension.

Moreover, administration of the non-halide potassium salt is believed to attenuate increases of blood pressure otherwise induced by dietary NaCl in salt-sensitive individuals. The non-halide potassium therapy thus protects salt-sensitive individuals against extreme blood pressure elevations which might otherwise occur when they are on high salt diets.

Also provided as part of the invention are methods for diagnosing individuals susceptible to or suffering from hypertension which is or will be amenable to treatment with a non-halide potassium salt.

DESCRIPTION OF THE FIGURES

FIG. 1 is a graph showing the results of administering 200 mmoles of potassium bicarbonate per 70 kg. body weight per day in four oral doses on each of 15 days to two male patients having essential hypertension. In the graph each patient's mean arterial pressure (MAP) is plotted against time for a pre-treatment "Control" period, a "KHCO$_3$" treatment period, and a "Recovery" period. Filled bars represent the differences between the control average MAP for the 10-day steady-state control period (represented by the horizontal line) for one patient, and unfilled bars represent the data for the second patient. Bars above the zero line indicate MAP values exceeding the control period average, and bars below the line indicate MAP values lower than the control period average;

FIG. 2 is a graph similar to FIG. 1, showing the results of administering approximately 100 mmoles of potassium bicarbonate per 70 kg. body weight per day for eight days to five normotensive males. The bar for each day represents the average change in the MAP value for the group from the control period; and FIG. 3 is another graph similar to FIGS. 1 and 2, containing separate plots of the average systolic and diastolic MAP values against time for six post-menopausal normotensive women.

DESCRIPTION OF THE PREFERRED EMBODIMENTS

In accordance with the present invention, novel methods are provided for preventing or ameliorating hypertension, which comprises administering to subjects a potassium salt in which the anion component is other than chloride or other halide in amounts sufficient to provide the desired physiological benefit while avoiding amounts sufficient to induce undesirable toxic effects.

As used herein, the terms "treatment" or "treating" relate to any treatment of hypertensive disease, and include: (1) preventing hypertension from occurring in a subject who may be predisposed to the disease but who has not yet been diagnosed as having it; (2) inhibiting the disease, i.e., arresting its development; or (3) ameliorating or relieving the symptoms of the disease, i.e., causing regression of the hypertensive state.

One hypothesis for the results achieved by the present treatment, offered by way of explanation but not limitation, is that the increase of chloride or other halide upon the administration of potassium chloride or the like, induces physiological changes that antagonize or otherwise counter or mask the anti-hypertensive effect of potassium. Accordingly, subjects who do not exhibit a lowering of blood pressure in response to the administration of potassium chloride or bromide may show a response to a non-halide salt of potassium, and patients who have shown some anti-hypertensive response to potassium chloride or bromide may show a substantially greater response when a non-halide potassium salt is used instead.

The non-halide potassium salts which may be employed in the process of the present invention are those which exhibit the ability to decrease the systolic or diastolic blood pressure of an individual without significant undesirable side effects. A number of pharmaceutically-acceptable salts are known, several of which are set forth in Berg et al., J. Pharmaceut. Sci. (1977) 66:1, which is incorporated herein by reference. It is known that the chloride ion acts as a pressor or contributes to the pressor effect in formulations of sodium chloride (Kurtz et al., N. Engl. J. Med. (1987) 317:1043, which is incorporated herein by reference). Given the disclosure herein, it will be well within the ability of one skilled in the art to select and screen pharmaceutically-acceptable potassium salts for the ability to lower blood pressure using well known methods and techniques. Desirably, a potassium salt will be selected which is therapeutically effective in amounts readily achievable in humans while being relatively well tolerated.

Different salts may be chosen depending on particular routes of administration and preferred modes of formulation. Additionally, it may be preferred to select potassium salts which, upon administration, produce a slight systemic alkalinization, which alkalinization itself may contribute to a vasodilatory effect that augments a specific vasodilatory effect conferred by the potassium ion. A bicarbonate component or metabolite generated promptly after administration or ingestion of the salt may thus not only alkalinize the blood, but it may affect the distribution of fluids between the vascular and extravascular compartments. Blood pH and bicarbonate levels may be determined using well accepted methods long known to those skilled in the arts.

The potassium salts which may be thus administered are preferably selected from the group consisting of potassium bicarbonate ($KHCO_3$), potassium phosphate ($K_2HPO_4$ or a mixture of $K_2HPO_4$ and $KH_2PO_4$), potassium gluconate ($C_6H_{11}KO_7$) and potassium citrate ($C_6H_5K_3O_7$). The use of potassium bicarbonate and potassium phosphate is particularly preferred in this invention.

The preparation, isolation and purification of these salts are well known to those skilled in the art, as they are commonly employed in a therapeutic setting for a variety of uses other than described herein. Specific preparation procedures for each salt are described in general terms in Remington's Pharmaceutical Sciences, Mack Publishing Company, Easton, Pa., 16th Ed., 1982, which is incorporated herein by reference.

Administration of a non-halide potassium salt as an active compound may be in a pharmaceutical composition described hereinafter and can be via any of the accepted modes of administration for agents which are known to affect hypertension. These methods include oral, parenteral, and other modes of systemic administration. Different non-halide potassium salts may be admixed and simultaneously administered, or benefit may be gained in some instances by their separate, sequential administration.

Depending on the intended mode, the compositions may be in the form of solid, semi-solid or liquid dosage forms, such as, for example, tablets, capsules, pills, powders, granules, crystals, liquids, suspensions, or the like, preferably in unit-dosage forms suitable for administration of relatively precise dosages. The compositions may include a conventional pharmaceutical carrier or excipient and, in addition, may include other medical agents, pharmaceutical agents, carriers, etc.

The amount of the non-halide potassium salt administered in accordance with the present invention will, of course, be dependent on the subject being treated, the severity of the affliction, the manner of administration, and the judgment of the prescribing physician. However, an effective dose of potassium bicarbonate, for instance, will be in the range of 50–300 mmoles/70 kg/day, preferably 50–250 mmoles/70 kg/day. Dosages may be adjusted by monitoring the effects of the amount administered and adjusting subsequent amounts as appropriate.

Many of the potassium salts of the invention may be administered in relatively large amounts without serious side effects, although indiscriminate use of potassium salts may produce toxic manifestations of hyperkalemia and gastrointestinal irritation. In cases where the compound is administered to prevent the emergence of hypertension in normotensive subjects susceptible to hypertension, or those suffering from only mild or borderline hypertension, the dose may be adjusted accordingly to lower maintenance levels.

For solid compositions, the non-halide potassium salts such as potassium bicarbonate may be provided separately or may be compounded with conventional nontoxic solid carriers such as, for example, pharmaceutical grades of mannitol, lactose, starch, magnesium stearate, talcum, cellulose, glucose, sucrose, magnesium carbonated, and the like. Liquid pharmaceutically-administrable compositions can be prepared, for example, by dissolving the salt, such as potassium bicarbonate, and optional pharmaceutical adjuvants in a carrier, such as, for example, water, aqueous dextrose, glycerol, and the like, to thereby form a solution or suspension. If desired, the pharmaceutical composition to be administered may also contain minor amounts of nontoxic auxiliary substances such as pH buffering agents and the like, for example, sorbitan monolaurate, triethanolamine, sodium acetate, triethanolamine oleate, etc. Actual methods of preparing such dosage forms are known, or will be apparent, to those skilled in this art; see, for example, Remington's Pharmaceutical Sciences, Mack Publishing Company, Easton, Pa., 16th Ed., 1982, which is incorporated herein by reference. The composition or formulation to be administered will, in any event, contain a quantity of the non-halide potassium salt in an amount effective to lower the systolic and/or diastolic blood pressure and alleviate or ameliorate the symptoms thereof or prevent their emergence in the subject being treated.

For oral administration, a pharmaceutically-acceptable nontoxic composition is formed by the incorporation of any of the normally employed excipients such as, for example, pharmaceutical grades of mannitol, lactose, starch, magnesium stearate, talcum, cellulose, glucose, sucrose, magnesium carbonate, and the like. Such compositions take the form of solutions, suspensions, tablets, pills, capsules, powders, granules, crystals, sustained-release formulations, and the like. Such compositions may contain about 10–100% active ingredient, preferably about 25–90%. As a dietary supplement potassium bicarbonate, for example, may be supplied as granules or powder and applied directly to foodstuffs or dissolved in drinking water as a convenient means of administration.

The compositions useful in the methods of the invention may be supplied in containers having printed instructions which direct the user to employ the compositions in the methods and for the purposes described herein. Accordingly, said containers having such instructions are considered part of the present invention. The instructions for use may be printed on the container or on a separate sheet which is included with the container. Among other things, the instructions, may for example, direct the user to employ the composition in addition to a normal dietary intake of salt, and may also state that the purpose of such method is to inhibit or otherwise prevent symptoms of or associated with hypertension. The instructions may be directed to normotensive individuals who may be predisposed to hypertension and/or to those already diagnosed as having essential hypertension.

The methods of the invention may also find use in diagnosing individuals suffering from or predisposed to hypertension. More particularly, typically a baseline blood pressure for an individual undergoing said diagnosis is first determined. Then a non-halide potassium salt useful in the present invention is administered according to the methods herein described. Usually the composition will be administered in an amount and for a time sufficient to produce a measurable lowering of blood pressure in individuals with hypertension or predisposed to developing hypertension and who may ultimately may be treatable with the therapeutic methods of the invention. If a person is thus identified as having a drop in blood pressure from the baseline, a physician may then elect to initiate an appropriate therapy or further monitor the patient.

The following examples illustrate some particularly preferred, non-limiting embodiments of the invention.

EXAMPLE 1

Effect of Potassium Bicarbonate in Hypertensive Patients

Studies were performed in two men (ages 55 and 57) with essential hypertension to demonstrate that a non-halide salt of potassium, potassium bicarbonate, lowered blood pressure. In both patients, hypertension was confirmed on at least three occasions in an out-patient setting after the patient had been sitting quietly for all least 10 minutes. In patient 1, the blood pressure ranged from 141/85 to 157/94 mm Hg; in patient 2, it-ranged from 144/93 to 156/100 mm Hg. Neither of the patients had clinical signs or symptoms of pheochromocytoma or renal-artery stenosis, and neither had clinical or laboratory evidence of impaired cardiac, renal, or hepatic function. Urinalysis and the serum concentrations of creatinine, sodium, and potassium were within normal limits in both.

All medications were stopped for each individual for at least four weeks before the beginning of the study. Both patients remained hospitalized throughout the study, where physical activity consisted only of daily walks. Throughout the study, each patient ate a constant amount of a nutritionally adequate whole-foods diet intrinsically low in sodium chloride (approximately 10 mmoles NaCl/70 kg body weight/day). A sodium chloride supplement was added in an amount sufficient to increase total sodium intake to 140 meq/day/70 kg. The diet also provided, per 70 kg/day, approximately 55 mmoles of potassium, 375 mg of calcium and 820 mg of phosphorus.

In each patient, the total number of calories provided was determined from the estimated amount of energy required to keep body weight constant. The diet contained, as a percentage of total calories, 35% fat, 56% carbohydrate, and 9% protein. The specific ingredients of each meal were constant throughout the study. Fluid intake was fixed at 3150 ml/70 kg/day.

A 10-day steady-state control period preceded the experimental period. Throughout the experimental period, both patients took an aqueous solution containing potassium bicarbonate, 1.0 mmoles/ml of solution; each patient ingested 200 mmoles of potassium bicarbonate/70 kg/day in three divided doses, with meals, on each day of the study, for a total of 15 days.

Blood pressure was measured in the nondominant arm at 8 A.M., Noon, 4 P.M., 8 P.M., and 10 P.M. of each day, with an automated oscillometric device (Dinamap, 1846P). In this manner, observer bias was avoided. At each measurement session, after the patient had been supine for 10 minutes, five measurements of systolic and diastolic pressure and heart rate were obtained and the average of the last four measurements were calculated. The measurements were repeated with the patient in the upright position at each session. The measurements were averaged to yield values for daily systolic and diastolic blood pressures. Mean arterial pressure was calculated as (systolic pressure–diastolic pressure)/3 +diastolic pressure.

The results of the study are shown in FIG. 1. The figure plots the difference of each day's mean arterial pressure (MAP) from the average MAP for the entire control period, represented by the horizontal zero line. Bars extending above the zero line indicate MAP values exceeding the control period average, and vice versa. Filled bars represent one patient, unfilled bars, the other.

Both patients had significant reductions in systolic, diastolic, and mean arterial pressures occurring promptly on initiating potassium bicarbonate treatment (day 1) and persisting for the 15-day treatment period. Heart rate increased during potassium bicarbonate treatment. Subject No. 1 manifested a significant rebound overshoot of blood pressure when the potassium bicarbonate was discontinued, and Subject No. 2 manifested a similar tendency early in the recovery period. No adverse effects of potassium bicarbonate administration were observed in either subject.

EXAMPLE 2

Effect of Potassium Bicarbonate in Normotensive Individuals

In a study performed similarly to that described in Example 1, the effect of potassium bicarbonate on the blood pressure in normotensive individuals was determined. The group consisted of five men, ages 40–53. The equilibration or control period consisted of 7 days, the treatment with potassium bicarbonate 8 days, and the recovery period an additional 8 days. Each subject ingested a daily potassium bicarbonate supplement of 100 meq/70 kg/day, making the total potassium intake approximately 150 meq/70 kg/day. The subjects were fed a diet having an intrinsic low-sodium chloride content (less than 10 meq sodium and chloride/day/ 70 kg body weight) and a normal potassium content (52 meq/day/70 kg body weight). A sodium chloride supplement was added sufficient to increase total sodium intake to 140 meq/70 kg/day.

The results of the study on the normotensive subjects is shown in FIG. 2. Each day's bar represents the groups' average change in mean arterial pressure from the control for that day. As with the hypertensive individuals, the administration of potassium bicarbonate resulted in significant reductions in mean arterial pressures, occurring promptly on initiating potassium bicarbonate treatment and persisting for the treatment period. The reduction in mean arterial pressures was also manifested during a portion of the recovery period. Thus potassium bicarbonate was shown to be effective in lowering blood pressure in normotensive individuals and may readily find prophylactive use in preventing the onset of hypertension in individuals identified as predisposed to the condition.

EXAMPLE 3

Effect of Potassium Bicarbonate in Normotensive Post-Menopausal Women

In six post-menopausal women (ages 52–65) who were not hypertensive, potassium bicarbonate was administered in an amount of 120 mmoles per kg body weight per day for 18 days. A significant and sustained reduction in both systolic and diastolic blood pressures resulted (see FIG. 3).

Blood pressures were measured without observer bias by use of an automated blood pressure reader-recorder, which in addition, gave improved accuracy by performing quadruplicate readings at each measurement session.

The studies were performed while the patients resided in the University of California General Clinical Research Center (Moffitt Hospital). Throughout the period of residence, the patients ate a constant diet of known composition, comprising (per 60 kg body weight) 546 mg calcium, 948 mg phosphorus, 60 meq sodium, and 56 meq potassium. A supplement of sodium chloride of 60 mmoles/day was provided, making total sodium intake 120 meq per 60 kg body weight per day. Fluid intake was fixed.

The subjects were allowed 10 days for their bodies to equilibrate and adapt to the fixed diet. There then followed, immediately and in succession, a 12-day control period (CONTROL) prior to initiation of $KHCO_3$ administration, an 18-day period of $KHCO_3$ administration, and a 12-day recovery period after discontinuation of $KHCO_3$.

FIG. 3 shows the changes in systolic (upper panel) and diastolic (lower panel) blood pressures. For each subject, the average value of systolic blood pressure for the entire CONTROL period was subtracted from each day's systolic blood pressure, thereby generating a "difference from CONTROL" value for every day of the study, including the individual control days. For each day of the study, the average of the daily "differences from CONTROL" were calculated for the entire group of six subjects, and those were plotted in the figure as vertical bars. Vertical bars extending below the zero line represent decreases in systolic blood pressure relative to the average control value; vertical bars extending above the zero line represent increases in systolic blood pressure relative to the control value. A similar procedure was used for diastolic blood pressure.

The $KHCO_3$ administration resulted in a prompt and sustained reduction in both systolic and diastolic blood pressures. After discontinuation of $KHCO_3$ the pressures gradually returned to control.

The results obtained in this experiment demonstrate that $KHCO_3$ lowers blood pressure in normotensive post-menopausal women.

From the foregoing, it will be appreciated that the present invention provides methods which effectively ameliorate/ prevent hypertension in humans. Because many of the non-halide potassium salts such as potassium bicarbonate are naturally-occurring and readily available, their use as a dietary supplement or otherwise present the possibility of a purely nutritional approach to hypertension, thereby avoiding the disadvantages of conventional pharmacological intervention.

Although the present invention has been described in some detail by way of illustration and example for purposes of clarity and understanding, it will be obvious that certain changes and modifications may be practiced within the scope of the appended claims.

What is claimed is:

1. A method for treating hypertension in a person on a diet having a normal range of salt content, which comprises:
   orally administering to such a person a composition containing at least one active ingredient for treating hypertension, a principal active ingredient being potassium bicarbonate and the composition being substantially free of potassium chloride, the potassium bicarbonate being administered in an amount sufficient to have a measurable blood pressure lowering effect on the person treated due to the presence of potassium bicarbonate but not in an amount sufficient to induce undesirable toxic effects.

2. The method of claim 1, for treating a person who has hypertension or a person who has normal blood pressure but is susceptible to hypertension, with said potassium bicarbonate-containing composition.

3. The method of claim 1, for treating a person who has hypertension with said potassium bicarbonate-containing composition.

4. The method of claim 1, wherein the composition is administered as a dietary supplement.

5. The method of claim 1, wherein the composition is administered in an amount containing from about 50–300 mmoles of the potassium bicarbonate/70 kg body weight/24 hours.

6. The method of claim 1, wherein the composition includes a pharmaceutically-acceptable carrier.

7. The method of claim 1, wherein the composition is substantially free of potassium chloride.

8. The method of claim 1, wherein potassium bicarbonate is substantially the only active ingredient for treating hypertension in said composition.

9. The method of claim 1, wherein the person is on a diet having a salt content ranging from a moderately-restricted salt intake of about 75 meq. of NaCl per day to a salt intake of about 300 meq. of NaCl per day or higher.

10. A method for treating hypertension in a person aged 40–65 who is on a diet having a normal range of salt content, which comprises orally administering to such a person a composition containing at least one active ingredient for treating hypertension, a principal active ingredient being potassium bicarbonate and the composition being substantially free of potassium chloride, the potassium bicarbonate being administered in an amount sufficient to have a measurable blood pressure lowering effect on the person treated due to the presence of potassium bicarbonate but not in an amount sufficient to induce undesirable toxic effects.

11. The method of claim 10, for treating a person who has hypertension or a person who has normal blood pressure but is susceptible to hypertension, with said potassium bicarbonate-containing composition.

12. The method of claim 10, for treating a person who has hypertension with said potassium bicarbonate-containing composition.

13. The method of claim 10, wherein the composition is administered as a dietary supplement.

14. The method of claim 10, wherein the composition is administered in an amount containing from about 50–300 mmoles of the potassium bicarbonate/70 kg body weight/24 hours.

15. The method of claim 10, wherein the composition includes a pharmaceutically-acceptable carrier.

16. The method of claim 10, wherein the composition is substantially free of potassium chloride.

17. The method of claim 10, wherein potassium bicarbonate is substantially the only active ingredient for treating hypertension in said composition.

18. The method of claim 10, wherein the person is on a diet having a salt content ranging from a moderately-restricted salt intake of about 75 meq. of NaCl per day to a salt intake of about 300 meq. of NaCl per day or higher.

19. A method of diagnosing hypertension in a person on a diet having a normal range of salt content, said person being susceptible to or suffering from hypertension, which comprises measuring such person's blood pressure to obtain a first value, orally administering to such a person a composition containing at least one active ingredient for treating hypertension, a principal active ingredient being potassium bicarbonate and the composition being substantially free of potassium chloride, the potassium bicarbonate being administered in an amount sufficient to have a measurable blood pressure lowering effect on the person's blood pressure due to the presence of potassium bicarbonate but not sufficient to induce undesirable toxic effects, measuring the person's blood pressure to obtain a second value, and comparing said first and second values to determine whether to initiate anti-hypertension therapy.

20. The method of claim 19, wherein said composition is administered in an amount and for a time sufficient to cause a measurable lowering of blood pressure in a person who is responsive to potassium bicarbonate therapy or prophylaxis.

21. The method of claim 19, wherein the composition is administered in an amount containing from about 50–300 mmoles of the potassium bicarbonate/70 kg body weight/24 hours.

22. The method of claim 19, wherein the composition is substantially free of potassium chloride.

23. The method of claim 19, wherein potassium bicarbonate is substantially the only active ingredient for treating hypertension in said composition.

24. The method for treating hypertension of claim 1, wherein the potassium bicarbonate is the principal active ingredient and is present in major amount.

25. The method for treating hypertension of claim 10, wherein the potassium bicarbonate is the principal active ingredient and is present in major amount.

26. The method of diagnosing hypertension of claim 19, wherein the potassium bicarbonate is the principal active ingredient and is present in major amount.

* * * * *